United States Patent [19]

Mookherjee et al.

[11] 4,267,076

[45] May 12, 1981

[54] PREPARATION OF A CARYOPHYLLENE ALCOHOL MIXTURE IN PERFUME COMPOSITIONS

[75] Inventors: Braja D. Mookherjee, Holmdel; Cynthia J. Mussinan, Bricktown; Manfred H. Vock, Locust; Joaquin F. Vinals, Red Bank, all of N.J.; Jacob Kiwala, Brooklyn, N.Y.; Frederick L. Schmitt, Holmdel, N.J.

[73] Assignee: International Flavors & Fragrances Inc., New York, N.Y.

[21] Appl. No.: 105,924

[22] Filed: Dec. 21, 1979

Related U.S. Application Data

[62] Division of Ser. No. 947,186, Sep. 29, 1978.

[51] Int. Cl.³ .......................... C11B 9/00; A11K 7/46
[52] U.S. Cl. ............................................... 252/522 R
[58] Field of Search ................................... 252/522 R

[56] References Cited

FOREIGN PATENT DOCUMENTS

2044018  1/1973  Fed. Rep. of Germany .

OTHER PUBLICATIONS

Schulte-Elte et al., Helv. Chim. Acta, 51, 494, 1968.
Tetrahedron, 27, 635, 1971.
Tetrahedron Letters, 8, 659, 1971.
S. Aritauder, Perfume and Flavor Chemicals, published by author, Montclair, N.J., Monograph 586, 1969.

*Primary Examiner*—Veronica O'Keefe
*Attorney, Agent, or Firm*—Arthur L. Liberman

[57] ABSTRACT

A process for preparing a mixture of isomers of caryophyllene alcohol and dihydrocaryophyllene alcohol including 10,10-dimethyl-2,6-dimethylene bicyclo[7.2.0]undecan-5-ol by isomerizing caryophyllene oxide or dihydrocaryophyllene oxide using an aluminum isopropylate catalyst in a toluene solvent at temperatures in the range of from about 100° C. up to about 150° C. is described.

1 Claim, 12 Drawing Figures

GLC PROFILE FOR EXAMPLE I FRACTIONS 7 & 8

PEAK 2
PEAK 1
PEAK 3

MASS SPECTRUM FOR EXAMPLE I, PEAK 1

FIG.3
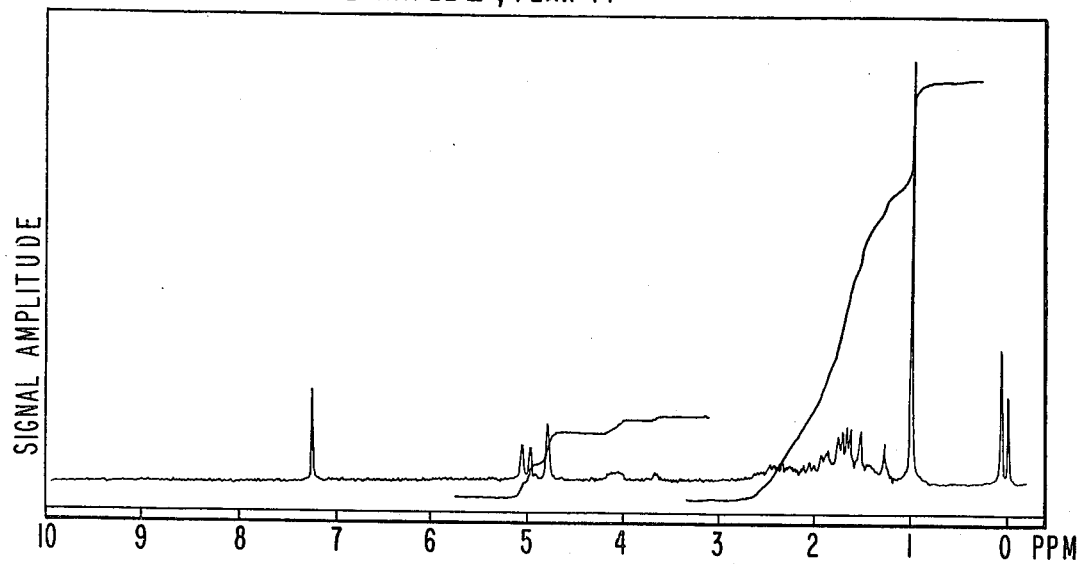
NMR SPECTRUM FOR EXAMPLE I, PEAK I.
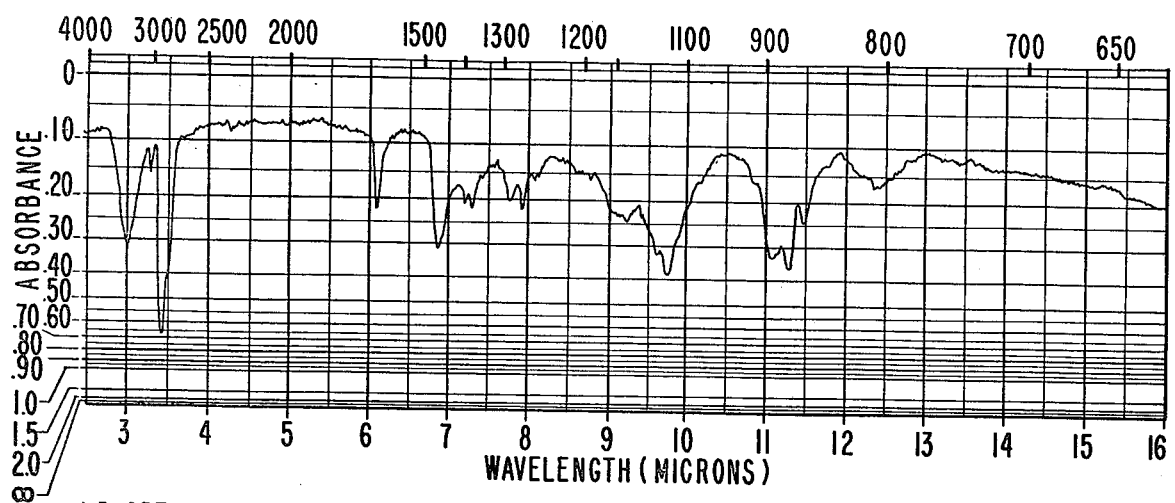
IR SPECTRUM FOR EXAMPLE I, PEAK I.
FIG.4

FIG.5
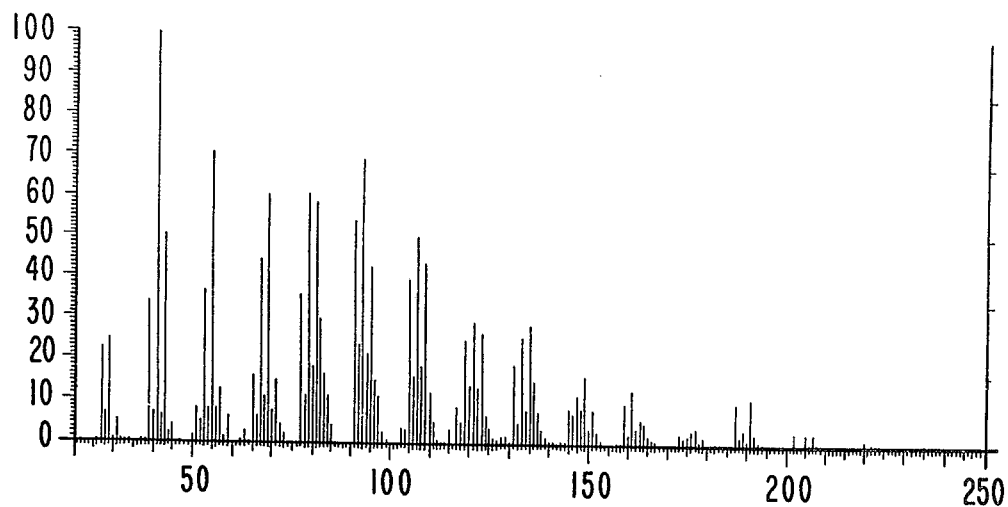
MASS SPECTRUM FOR EXAMPLE I, PEAK 2.
NMR SPECTRUM FOR EXAMPLE I, PEAK 2.
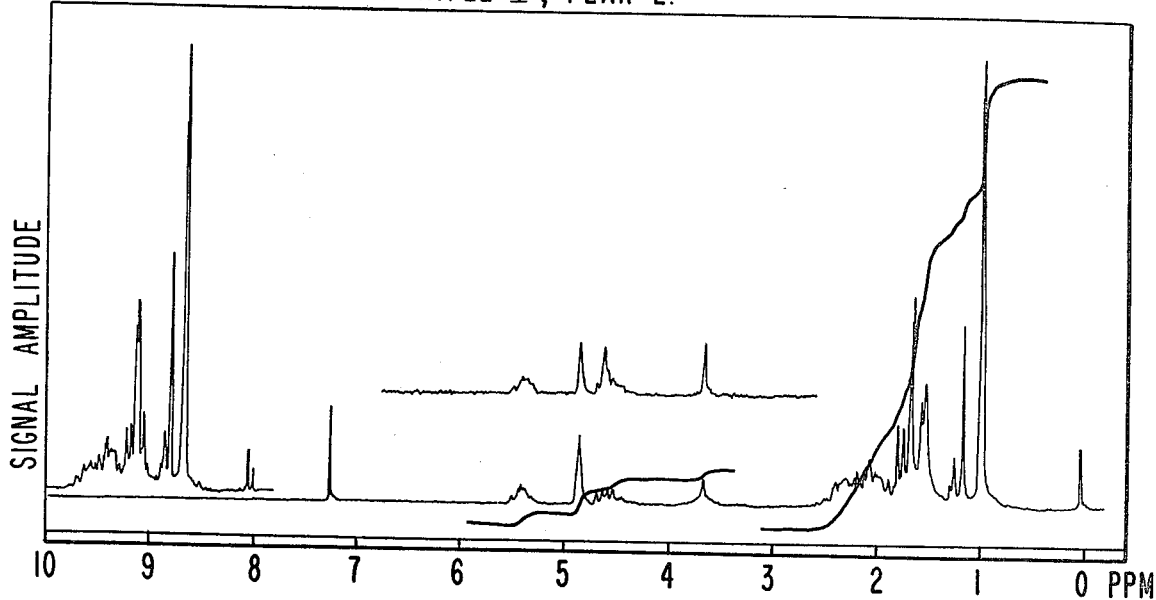
FIG.6

FIG.7
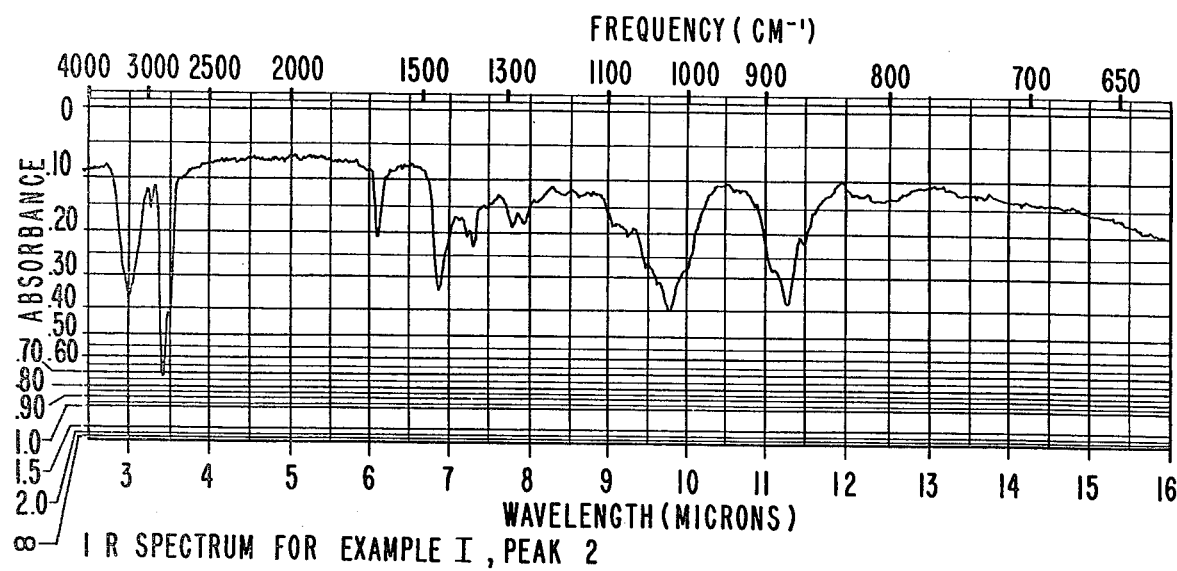
IR SPECTRUM FOR EXAMPLE I, PEAK 2
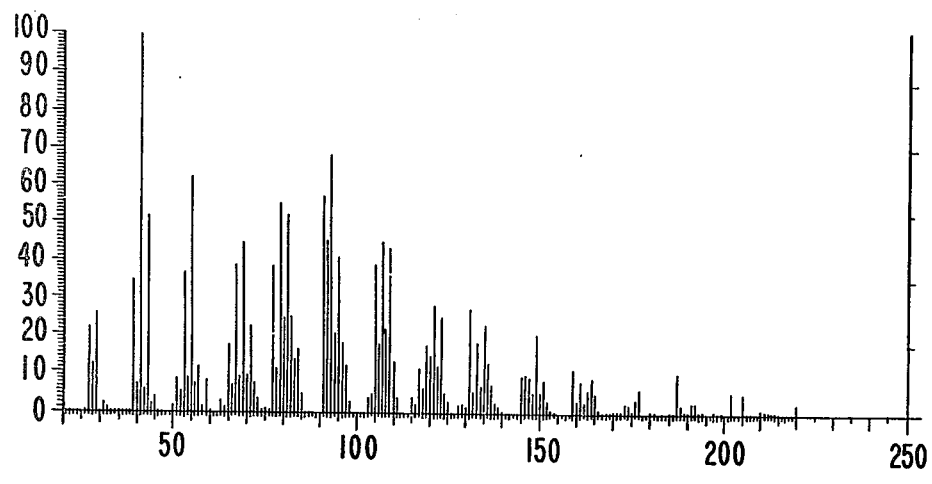
MASS SPECTRUM FOR EXAMPLE I, PEAK 3.
FIG.8

NMR SPECTRUM FOR EXAMPLE I, PEAK 3.

IR SPECTRUM FOR EXAMPLE I, PEAK 3.

FIG.11
GLC PROFILE FOR EXAMPLE II, FRACTION 8.
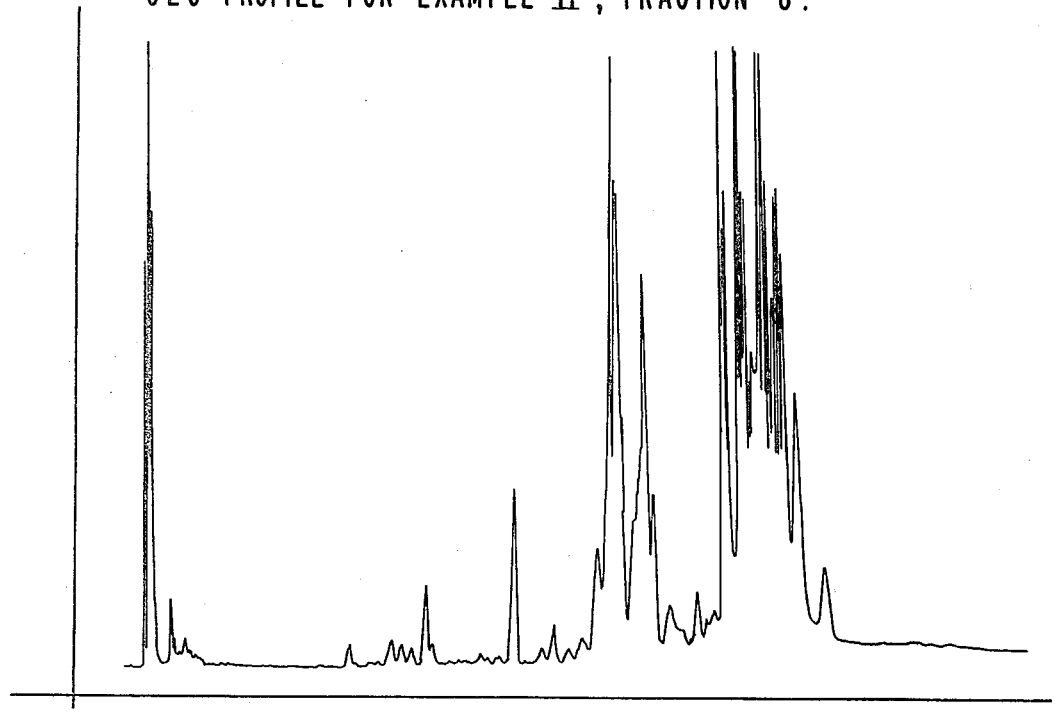
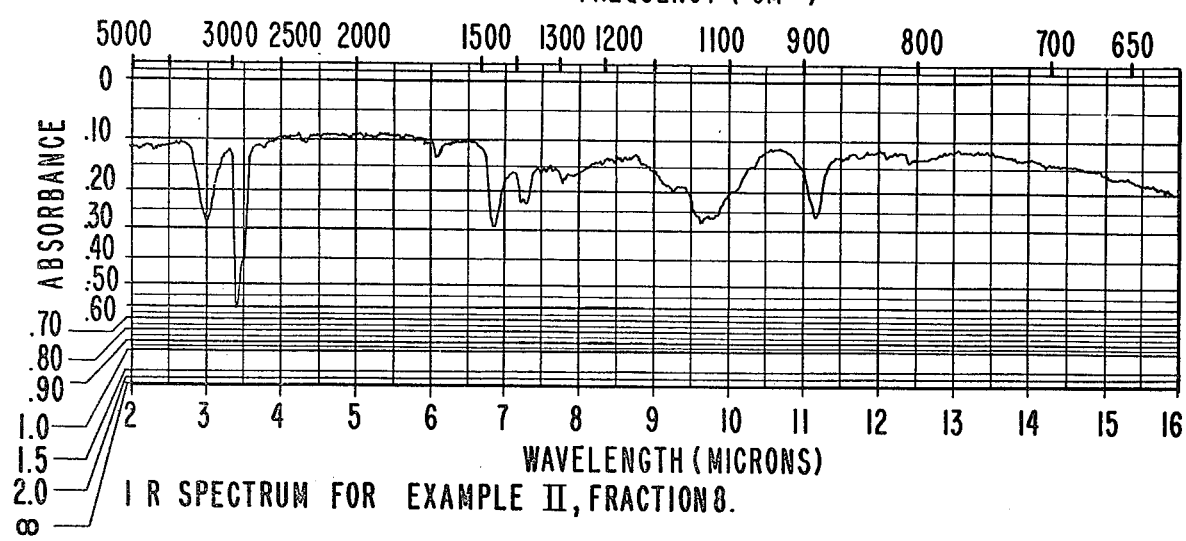
IR SPECTRUM FOR EXAMPLE II, FRACTION 8.
FIG.12

PREPARATION OF A CARYOPHYLLENE ALCOHOL MIXTURE IN PERFUME COMPOSITIONS

This application is a divisional of Application for United States Letters Patent, Ser. No. 947,186, filed on Sept. 29, 1978, now United States Patent issued on.

BACKGROUND OF THE INVENTION

This invention concerns an improved process of preparing isomers of caryophyllene alcohols and dihydro caryophyllene alcohols. More specifically, this invention is concerned with preparation of a specific isomer mixture range of caryophyllene alcohols and dihydro caryophyllene alcohols by means of the catalytic isomerization of caryophyllene oxide and dihydro caryophyllene oxide.

Swiss Pat. No. 549,960, issued on Apr. 30, 1974, as well as U.S. Pat. Nos. 4,014,350 (issued on Mar. 29, 1977); 3,840,023 (issued on Oct. 8, 1974) and 3,937,228 (issued on Feb. 10, 1976) disclose the organoleptic utility of isomers of caryophyllene alcohol produced according to our invention in oriental tobacco. The structures of these caryophyllene alcohol isomers are:

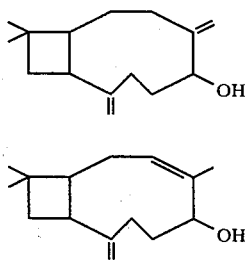

It is indicated in said Swiss Pat. No. 549,960 that these materials may be prepared according to the procedure set forth in Helv. Chim. Acta, 51, 494 (1968) Schulte-Elte and Ohloff. In this article it is indicated that the dye-sensitized photooxygenation of isocaryophyllene leads to formation of several alcohols having the structures:

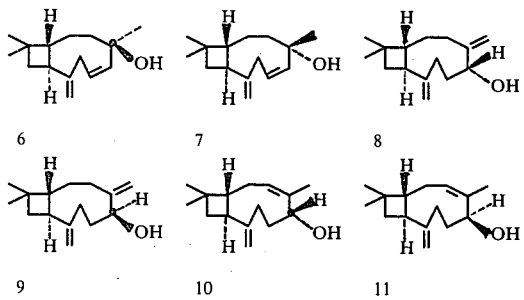

The reaction to convert carophyllene oxide to various isomer mixtures of alcohols is also disclosed in Tetrahedron 27, 635 (1971) and Tetrahedron Letters 8 659 (1971) whereby the reaction:

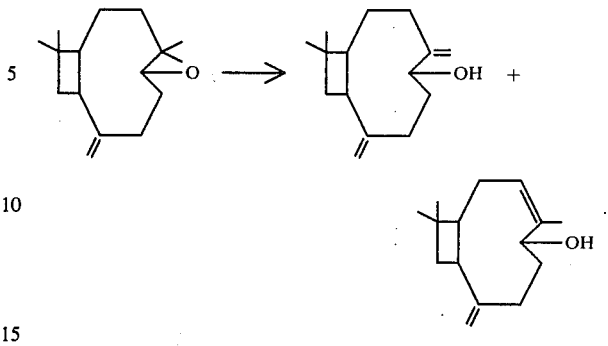

is carried out; in Tetrahedron 27 using an aluminum oxide catalyst and in Tetrahedron Letters 8 using a pyridinium bromide/pyridine catalyst system.

Nothing in the prior art, however, discloses our process for producing the caryophyllene alcohol isomer mixtures or the dihydro caryophyllene alcohol mixtures of our invention whereby a fast commercially feasible reaction takes place without the use of any noxious solvents (e.g., pyridine) and nothing in the prior art discloses the specific reaction product mixtures produced according to the process of our invention.

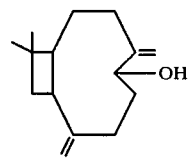

FIG. 3 is the NMR spectrum for peak 1 of the caryophyllene alcohol mixture produced according to Example I.

FIG. 4 is the IR spectrum for peak 1 of the caryophyllene alcohol mixture produced according to Example I.

FIG. 5 is the mass spectrum for peak 2 of the caryophyllene alcohol mixture produced according to Example I which caryophyllene alcohol has one of the structures:

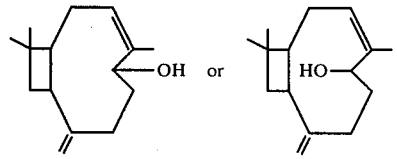

FIG. 6 is the NMR spectrum for peak 2 of the caryophyllene alcohol mixture produced according to Example I having one of the structures:

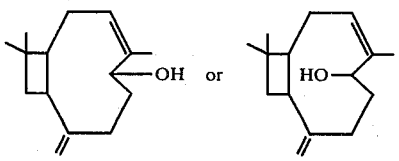

FIG. 7 is the infrared spectrum for peak 2 of the caryophyllene alcohol mixture produced according to Example I having one of the structures:

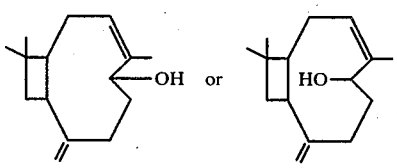

FIG. 8 is the mass spectrum for peak 3 of the caryophyllene alcohol mixture produced according to Example I having one of the structures:

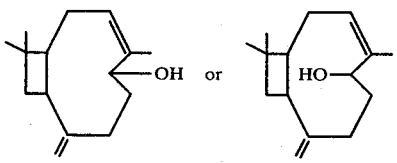

Figure 9:
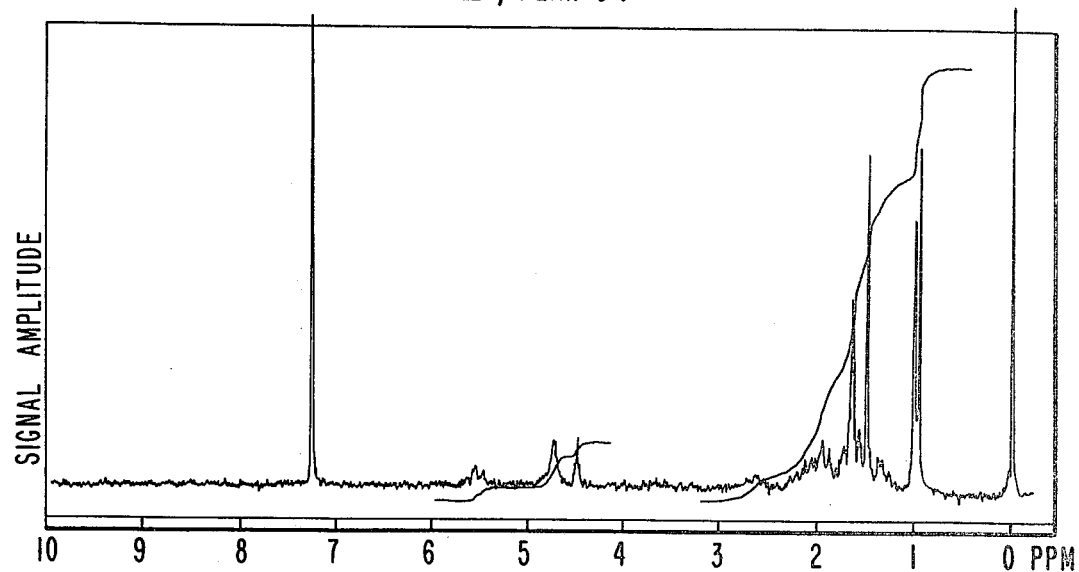

FIG. 9 is the NMR spectrum for peak 3 of the caryophyllene alcohol mixture produced according to Example I having one of the structures:

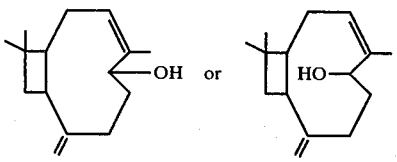

Figure 10:
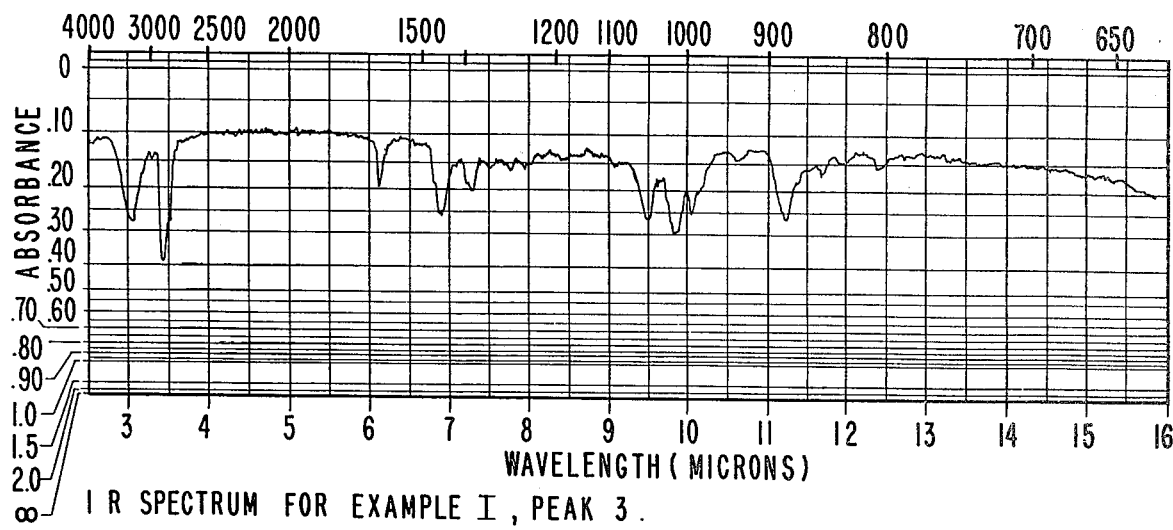

FIG. 10 is the infrared spectrum for peak 3 of the caryophyllene alcohol mixture produced according to Example I having one of the structures:

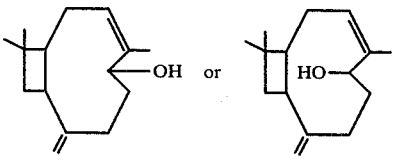

FIG. 11 is the GLC profile for the reaction product of Example II, fraction 8.

FIG. 12 is the infrared spectrum for fraction 8 of the reaction product produced according to Example II.

THE INVENTION

The invention relates to a process for preparing caryophyllene alcohol mixtures from caryophyllene oxide according to the reaction scheme:

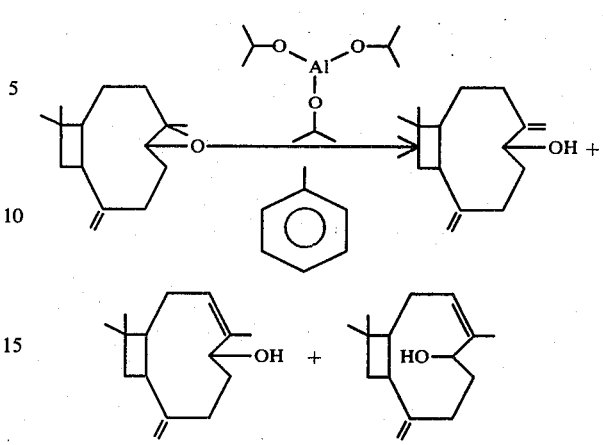

or a dihydro caryophyllene alcohol mixture from dihydro caryophyllene according to the reaction scheme:

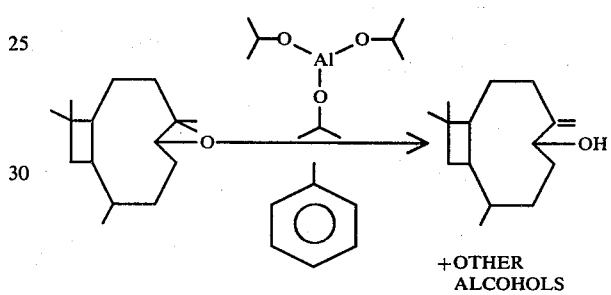

+OTHER ALCOHOLS using an aluminum isopropylate/toluene catalyst system.

The caryophyllene alcohol mixtures and dihydro caryophyllene alcohol mixtures produced according to our invention have musky, oriental sandalwood aroma and flavor characteristics causing them to be useful in raspberry, peach, apricot and blackberry flavors. In addition the caryophyllene alcohol mixture of our invention has a sweet, woody, peppery aroma with sweet, woody topnotes and slight borneol background causing it to be extremely useful in the perfume composition field and causing it to be useful for incorporation into perfumed articles such as soaps and detergents. The structures of the three caryophyllene alcohol isomers produced according to our invention are:

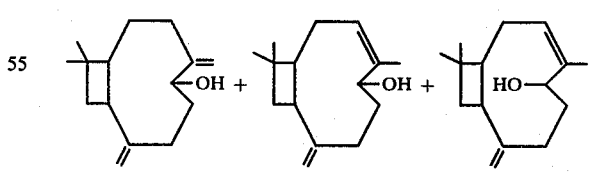

In accordance with the present invention, it has now been found that the novel mixtures of caryophyllene alcohols and dihydro caryophyllene alcohols of our invention may be prepared from caryophyllene oxide and dihydro caryophyllene oxide by treatment of the caryophyllene oxide or dihydro caryophyllene oxide at elevated temperatures with an aluminum isopropylate/toluene catalyst system.

As will be seen from Table I in Example I, the amounts of isomers of the three caryophyllene alcohols prepared from caryophyllene oxide having the structures:

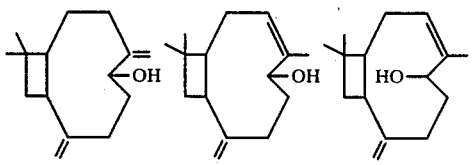

will vary from about 30:65:5 to 8:40:30.

It is preferable that the reaction be carried out at temperatures between 100° C. and 150° C. with reflux temperatures at atmospheric pressure being preferred (e.g. 110°–112° C.). The concentration of aluminum isopropylate catalyst in the reaction mass may vary from about 0.025 molar up to about 0.75 molar with a preferred concentration of aluminum isopropylate being about 0.04–0.10 molar. The concentration of caryophyllene oxide or dihydro caryophyllene oxide in the reaction mass may vary from about 0.25 molar up to about 1.00 molar with a preferred concentration of caryophyllene oxide or dihydro caryophyllene oxide being from 0.40 and 0.50 molar.

The reaction time is dependent on the temperature of reaction to a great extent. However, it is preferred that a reaction time of from about 1 up to about 5 hours be used in carrying out this reaction. Additional time of reaction does not improve the yield and a shorter reaction time gives rise to a much lower yield. At temperatures above about 150° C. the catalyst loses its effectiveness and undesirable side reactions or degradation of the caryophyllene alcohol or dihydro caryophyllene alcohol reaction product and caryophyllene oxide or dihydro caryophyllene oxide reactant may occur.

Atmospheric, subatmospheric or above atmospheric pressures can be used, although for reasons of convenience, substantially atmospheric pressures are preferred.

The caryophyllene alcohols and dihydro caryophyllene alcohols obtained can readily be recovered by conventional techniques. Thus, the toluene solvent employed is removed on a rotary evaporator. The residue is then subjected to "Rushover" distillation or fractional distillation which will yield the desired fractions containing the three caryophyllene alcohol isomers or the several dihydro caryophyllene alcohol isomers in the desired isomer ratio.

When the caryophyllene alcohol or dihydrocaryophyllene alcohol isomer mixture of our invention are used as food flavor adjuvants, the nature of the co-ingredients included with each of the said caryophyllene alcohol or dihydrocaryophyllene alcohol isomer mixture of our invention in formulating the product composition will also serve to alter, modify, augment or enhance the organoleptic characteristics of the ultimate foodstuff treated therewith.

As used here in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add additional flavor notes.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble, chewable plastic gum base such as chicle, or substitutes therefor, including jelutong, guttakay, rubber or certain comestible natural or synthetic resins or waxes. Incorporated with the gum base in admixture therewith may be plasticizers of softening agents, e.g., glycerine; and a flavoring composition which incorporates one or more of the caryophyllene alcohol or dihydrocaryophyllene alcohol isomer mixture of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxyanisole), butylated hydroxytoluene (2,6-di-tertiary-butyl-4-methylphenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins, and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include aldehydes, esters, natural oils, alcohols, sulfides, ketones, lactones, carboxylic acids and hydrocarbons such as heliotropin, terpinenol-4, benzaldehyde, anisaldehyde, phenyl acetaldehyde, benzyl formate, benzyl acetate, cis-3-hexenyl benzoate, methyl hexanoate, hexanal, eucalyptol, eugenol, acetaldehyde, ethyl acetate, ethyl butyrate, turpentine gum oil, limonene, gum camphor, isobornyl acetate, borneol, cinnamic aldehyde, cuminic aldehyde, furfural, methyl cinnamate, cassia oil, vanillin, maltol, parahydroxybenzyl acetone, dimethyl sulfide, alpha-ionone, acetic acid, isobutyl acetate, acetone, butyric acid, formic acid, valeric acid, amyl acetate, amyl butyrate, anethol, benzyl salicylate, diacetyl, dimethyl anthranilate, ethyl methylphenylglycidate, ethyl succinate, ethyl valerate, geraniol, cis-3-hexen-1-ol, 2-hexenyl acetate, 2-hexenyl butyrate, hexyl butyrate, 4-(p-hydroxyphenyl)-2-butanone, beta-ionone, isobutyl cinnamate, jasmine, lemon essential oil, methyl butyrate, methyl caproate, methyl disulfide, methylp-naphthyl ketone, orris butter, rose absolute, terpinyl acetate, gamma-undecalactone, vanilla and alcohol.

The specific flavoring adjuvant selected for use may be either solid or liquid depending upon the desired physical form of the ultimate product, i.e., foodstuff, whether simulated or natural, and should, in any event, (i) be organoleptically compatible with the caryophyllenealcohol or dihydrocaryophyllene alcohol isomer mixture of our invention by not covering or spoiling the organoleptic properties (aroma and/or taste) thereof; (ii) be nonreactive with the caryophyllene alcohol or dihydrocaryophyllene alcohol isomer mixture of our invention and (iii) be capable of providing an environment in which the caryophyllene alcohol or dihydrocaryophyllene alcohol isomer mixture of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of caryophyllene alcohol or dihydrocaryophyllene alcohol isomer mixture of our invention employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas, relatively minor quantities may suffice for purposes of enhancing the composition merely deficient in natural flavor or aroma. The primary requirement is that the amount selected to be effective, i.e., sufficient to alter, modify or enhance the organoleptic characteristics of the parent composition, whether foodstuff per se, chewing gum, per se, medicinal product per se, toothpaste per se, or flavoring composition.

The use of insufficient quantities of caryophyllene alcohol or dihydrocaryophyllene alcohol isomer mixture of our invention will, of course, substantially vitiate any possibility of obtaining the desired results while excess quantities prove needlessly costly and, in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of caryophyllene alcohol or dihydrocaryophyllene alcohol isomer mixture of our invention ranging from a small but effective amount, e.g., 0.5 parts per million up to about 500 parts per million based on total composition are suitable. Concentrations in excess of the maximum quantity stated are not normally recommended, since they fail to provide commensurate enhancement of organoleptic properties. In those instances, wherein the caryophyllene alcohol or dihydrocaryophyllene alcohol isomer mixture of our invention are added to the foodstuff as an integral component of a flavoring composition, it is, of course, essential that the total quantity of flavoring composition employed be sufficient to yield an effective caryophyllene derivative concentration in the foodstuff product.

Food flavoring compositions prepared in accordance with the present invention preferably contain the caryophyllene alcohol or dihydrocaryophyllene alcohol isomer mixture of our invention in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the caryophyllene alcohol or dihydrocaryophyllene alcohol isomer mixture of our invention with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix are obtained by mixing the dried solid components, e.g., starch, sugar and the like and caryophyllene derivatives in a dry blender until the requisite degree of uniformity is achieved.

It is presently preferred to combine with the caryophyllene alcohol or dihydrocaryophyllene alcohol isomer mixture of our invention, the following adjuvants:

Heliotropin;
Terpinenol-4;
Benzaldehyde;
Anisaldehyde;
Phenyl acetaldehyde;
Benzyl formate;
Benzyl acetate;
Cis-3-hexenyl benzoate;
Methyl hexanoate;
Hexanal;
Eucalyptol;
Eugenol;
Acetaldehyde;
Ethyl acetate;
Ethyl butyrate;
Turpentine gum oil;
Limonene;
Gum camphor;
Isobornyl acetate;
Borneol;
Cinnamic aldehyde;
Cuminic aldehyde;
Furfural;
Methyl cinnamate;
Cassia oil;
Vanillin;
Maltol;
Parahydroxybenzylacetone;
Dimethyl sulfide;
Alpha-ionone;
Acetic acid;
Isobutyl acetate;
Acetone;
Butyric acid;
Formic acid;
Valeric acid;
Amyl acetate;
Amyl butyrate;
Anethol;
Benzyl salicylate;
Diacetyl;
Dimethyl anthranilate;
Ethyl methylphenylglycidate;
Ethyl succinate;
Ethyl valerate;
Geraniol;
Cis-3-hexen-1-ol;
2-Hexenyl acetate;
2-Hexenyl butyrate;
Hexyl butyrate;
4-(p-Hydroxyphenyl)-2-butanone;
Beta-ionone;
Isobutyl cinnamate;
Jasmine;
Lemon essential oil;
Methyl butyrate;
Methyl capronate;
Methyl disulfide;
Methyl p-naphthyl ketone;
Orris butter;
Rose absolute;
Terpinyl acetate;
Gamma-undecalactone;
Vanilla; and
Alcohol.

An additional aspect of our invention provides an organoleptically improved smoking tobacco product and additives therefor, as well as methods of making the same which overcome problems heretofore encountered in which specific desired woody, cigar-box-like and oriental tobacco-like flavor characteristics of natural "Turkish" tobacco (prior to smoking and, on smoking, in the mainstream and in the sidestream) are created or enhanced or modified or augmented and may be readily controlled and maintained at the desired uniform level regardless of variations in the tobacco components of the blend.

This invention further provides improved tobacco additives and methods whereby various desirable natural turkish type tobacco flavoring characteristics with woody, cigar-box and oriental notes may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient one or more caryophyllene alcohol or dihydrocaryophyllene alcohol isomer mixture of our invention.

In addition to the caryophyllene alcohol dihydrocaryophyllene alcohol isomer mixture of our invention other flavoring aroma additives may be added to the smoking tobacco material or substitute therefor either separately or in mixture with the caryophyllene alcohol or dihydrocaryophyllene alcohol isomer mixture of our invention as follows:

I. Synthetic Materials:
Beta-ethyl-cinnamaldehyde;
Eugenol;
Dipentene;
Damascenone;
Maltol;
Ethyl maltol;
Delta undecalactone;
Delta decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropylacetophenone;
2-Hydroxy-2,5,5,8a-tetramethyl-1-(2-hydroxyethyl)-decahydronaphthalene;
Dodecahydro-3a,6,6,9a-tetramethyl-naphtho-(2,1-b)-furan 4-Hydroxyhexanoic acid, gamma lactone; and
Polyisoprenoid hydrocarbons defined in Example V of U.S. Pat. No. 3,589,372 issued on June 29, 1971.

II. Natural Oils:
Celery seed oil;
Coffee extract;
Bergamot Oil;
Cocoa extract;
Nutmeg Oil; and
Origanum Oil.

An aroma and flavoring concentrate containing one or more caryophyllene alcohol or dihydrocaryophyllene alcohol isomer mixture of our invention and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material substitutes (e.g., lettuce leaves) or mixtures thereof. The proportions of flavoring additives may be varied in accordance with taste but insofar as enhancement or the imparting of woody notes, and/or cigar box-like notes and/or oriental notes, we have found that satisfactory results are obtained if the proportion by weight of the sum total of caryophyllene alcohol or dihydrocaryophyllene alcohol isomer mixture of our invention to smoking tobacco material is between 50 ppm, and 1,500 ppm (0.015%–0.15%). We have further found that satisfactory results are obtained if the proportion by weight of the sum total of caryophyllene alcohol or dihydrocaryophyllene alcohol isomer mixture of our invention used to flavoring material is between 1,500 and 15,000 ppm (0.15%–1.5%).

Any convenient method for incorporating the caryophyllene alcohol or dihydrocaryophyllene alcohol isomer mixture of our invention into the tobacco product may be employed. Thus, the caryophyllene alcohol or dihydrocaryophyllene alcohol isomer mixture of our invention taken alone or along with other flavoring additives may be dissolved in a suitable solvent such as ethanol, diethyl ether and/or volatile organic solvents and the resulting solution may either be spread on the cured, cased and blended tobacco material or the tobacco material may be dipped into such solution. Under certain circumstances, a solution of the caryophyllene alcohol or dihydrocaryophyllene alcohol isomer mixture of our invention taken alone or taken further together with other flavoring additives set forth above, may be applied by means of a suitable applicator such as a brush or roller on the paper or leaf wrapper for the smoking product, or it may be applied to the filter by either spraying, or dipping, or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the caryophyllene alcohol or dihydrocaryophyllene alcohol isomer mixture of our invention in excess of the amounts or concentrations above indicated so that when blended with other tobaccos, the final product will have the percentage within the indicated range.

In accordance with one specific example of our invention, an aged, cured and shredded domestic burley tobacco is sprayed with a 20% ethyl alcohol solution of dihydrocaryophyllene alcohol mixture including compounds having the structure:

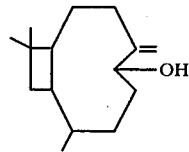

in an amount to provide a tobacco composition containing 800 ppm by weight of dihydrocaryophyllene alcohol mixture (produced according to Example II) on a dry basis. Thereafter, the ethyl alcohol is removed by evaporation and the tobacco is manufactured into cigarettes by the usual techniques. The cigarette when treated as indicated has a desired and pleasing aroma which is detectable in the main and sidestreams when the cigarette is smoked. This aroma is described as being woody and oriental with a cigar box nuance.

While our invention is particularly useful in the manufacture of smoking tobacco, such as cigarette tobacco, cigar tobacco and pipe tobacco, other tobacco products, formed from sheeted tobacco dust or fines may also be used. Likewise, the caryophyllene alcohol or dihydrocaryophyllene alcohol isomer mixture of our invention can be incorporated with materials such as filter tip materials (e.g., cellulose acetate filters wherein woody oriental and cigar box-like effects are desired), seam paste, packaging materials and the like which are used along with tobacco to form a product adapted for smoking. Furthermore, the caryophyllene alcohol or dihydrocaryophyllene alcohol isomer mixture can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

The caryophyllene alcohol or dihydrocaryophyllene alcohol isomer mixture and one or more auxiliary perfume ingredients, including, for example, hydrocarbons, alcohols other than those having structures of the dihydrocaryophyllene alcohols and caryophyllene alcohols or our invention, ketones, aldehydes, nitriles, esters, lactones or cyclic esters, synthetic essential oils and natural essential oils, may be admixed so that the combined odors of the individual components produce a pleasant and desired fragrance, particularly and preferably in sweet, woody, and peppery fragrances. Such perfume compositions usually contains (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however the over-all sensory effect of the perfume composition will be at least the sum total of the effects of each of the ingredients. Thus, one or more of the caryophyllene alcohol or dihydrocaryophyllene alcohol isomer mixture of our invention can be used to alter, modify or enhance the aroma characteristics of a perfume composition, for example, by utilizing or moderating the olfactory reaction contributed by another ingredient in the composition.

The amount of caryophyllene alcohol or dihydrocaryophyllene alcohol isomer mixture of out invention which will be effective in perfume compositions as well as in perfumed articles and colognes depends on many factors, including the other ingredients, their amounts and the effects which are desired. It has been found that perfume compositions containing as little as 0.01% of caryophyllene alcohol or dihydrocaryophyllene alcohol isomer mixture or even less (e.g., 0.005%) can be used to impart a sweet, woody, peppery odor with borneol-like nuances to soaps, cosmetics, detergents (including anionic, non-ionic and cationic detergents), solid or liquid fabric softeners (e.g., "BOUNCE ®" a registered trademark of the Proctor and Gamble Company of Cincinnati, Ohio), laundry dryer brighteners or other products. The amount employed can range up to 70% of the fragrance components and will depend on considerations of cost, nature of the end product, the effect desired on the finished product and the particular fragrance sought.

The caryophyllene alcohol or dihydrocaryophyllene alcohol isomer mixture of our invention are useful (taken alone or together with other ingredients in perfume compositions) in detergents and soaps, space odorants and deodorants, laundry dryer brighteners, solid or liquid fabric softeners, perfumes, colognes, toilet water, bath preparations, such as lacquers, brilliantines, pomades and shampoos; cosmetic preparations, such as creams, deodorants, hand lotions and sun screens; powders, such as talcs, dusting powders, face powders and the like. As little as 1% of caryophyllene alcohol or dihydrocaryophyllene alcohol isomer mixture will suffice to impart an intense piney note to woody perfume formulations. Generally, no more than 3% of caryophyllene alcohol or dihydrocaryophyllene alcohol isomer mixture based on the ultimate end product, is required in the perfume composition.

In addition, the perfume composition or fragrance composition of our invention can contain a vehicle, or carrier for the caryophyllene alcohol or dihydrocaryophyllene alcohol isomer mixture. The vehicle can be a liquid such as a non-toxic alcohol, a non-toxic glycol, or the like. The carrier can also be an absorbent solid, such as a gum (e.g. gum arabic), or components for encapsulating the composition as by coacervation (such as gelatin).

It will thus be apparent that the caryophyllene alcohol or dihydrocaryophyllene alcohol isomer mixture of our invention can be utilized to alter, modify or enhance sensory properties, particularly organoleptic properties, such as flavor(s) and/or fragrance(s) of a wide variety of consumable materials.

The following examples serve to illustrate specific embodiments of our invention.

It will be understood that these Examples are illustrative and the invention is to be considered restricted thereto only as indicated in the appended claims.

All parts and percentages given herein are by weight unless otherwise specified.

EXAMPLE I

Preparation of Caryophyllene Alcohol Isomer Mixtures

Reaction

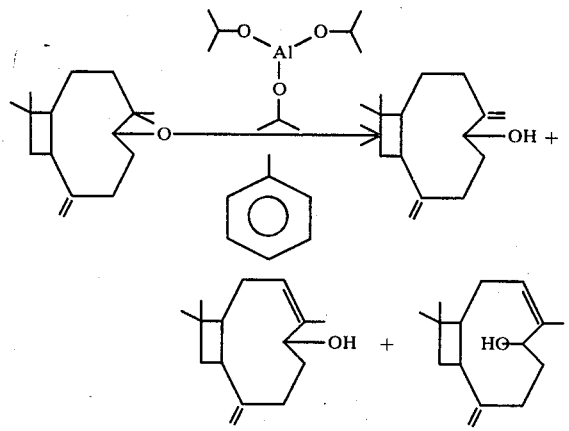

Chemicals

| | |
|---|---|
| caryophyllene oxide | 102 g (.46M) |
| aluminum isopropoxide | 10.2 g (.05M) |
| toluene | 100 cc |
| sulfuric acid (10%) | 100 cc |
| methylene chloride | 100 cc |
| sodium carbonate | 10 g |
| sodium sulfate | 10 g |

Equipment 500 ml 3-neck reaction flask
Friedrichs condenser
mechanical stirrer
thermometer
heating mantle Procedure Caryophyllene oxide, aluminum isopropoxide, and toluene are charged to a 500 ml three-neck flask equipped with a thermometer, mechanical stirrer and Friedrichs condenser. The mixture is heated to reflux (111° C.) with stirring for a period of 2.5 hours. After cooling to room temperature, 100 cc of cold 10% aqueous sulfuric acid are added, and the reaction mass is stirred for a period of 15 minutes. The resulting organic phase is separated, and the aqueous phase is extracted with two 50 cc portions of methylene chloride. The combined organic phases are washed with water, saturated aqueous sodium carbonate (approximately 100 cc), and then water again until neutral. After drying over anhydrous sodium sulfate, the toluene solvent is removed on a rotary evaporator under vacuum.

The resulting product (3 components) is purified by distillation through a 30 cm Vigreux column yielding the following fractions:

TABLE I

| Fraction No. | Vapor Temp. | Liquid Temp. | Vacuum mm Hg | pk 1 | pk 2 | pk 3 | Total | Weight(g) |
|---|---|---|---|---|---|---|---|---|
| 1 | 31 | 51 | 51 | | | | | 41.5 |
| 2 | 115 | 150 | 3.2 | | | | | 5.4 |
| 3 | 135 | 146 | 3.2 | | | | | 7.0 |
| 4 | 136 | 146 | 3.2 | 27.7 | 43.4 | 7.0 | 78.1 | 10.8 |

TABLE I-continued

| Fraction No. | Vapor Temp. | Liquid Temp. | Vacuum mm Hg | pk 1 | pk 2 | pk 3 | Total | Weight(g) |
|---|---|---|---|---|---|---|---|---|
| 5 | 139 | 150 | 3.3 | 28.9 | 54.0 | 7.5 | 90.4 | 2.8 |
| 6 | 135 | 157 | 3.5 | 27.2 | 58.5 | 9.1 | 94.8 | 8.6 |
| 7 | 140 | 155 | 3.5 | 22.9 | 62.8 | 12.4 | 98.1 | 5.5 |
| 8 | 142 | 155 | 2.8 | 20.4 | 57.3 | 22.0 | 99.7 | 25.1 |
| 9 | 125 | 190 | 2.8 | 8.3 | 59.9 | 29.3 | 97.5 | 1.2 |

Figure 1:
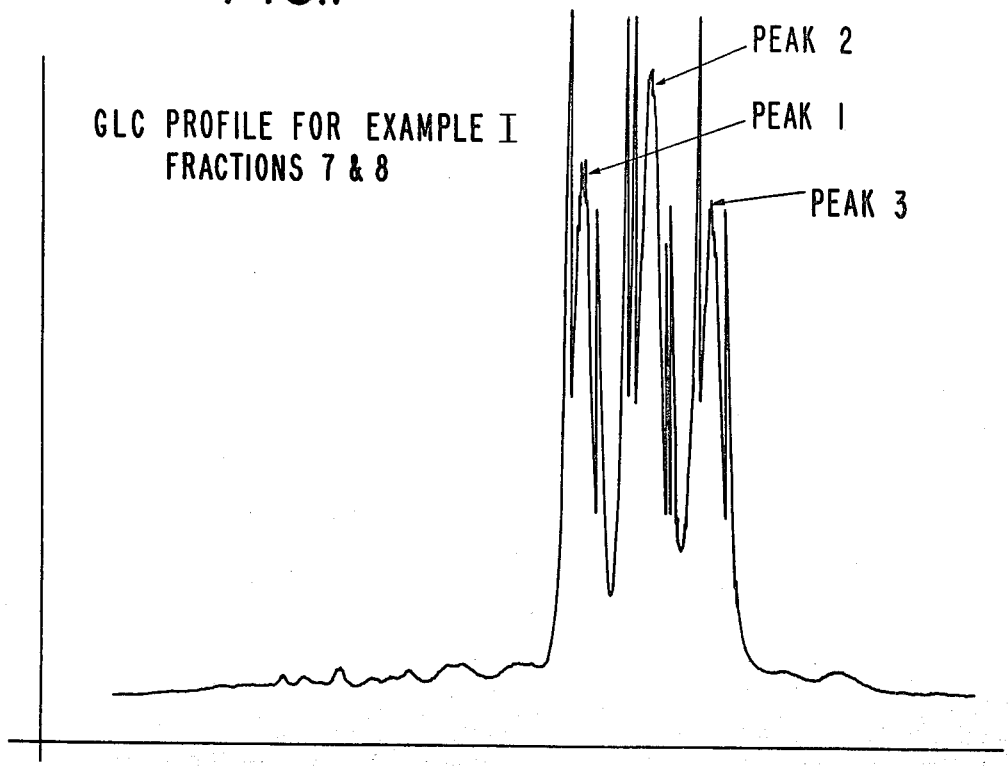
FIG. 1 is the GLC profile for the caryophyllene alcohol mixture produced according to Example I, fractions 7 and 8.

The yield of product greater than 94.8% pure is 40.4 grams or 39.9%. Fractions 7 and 8 are bulked and evaluated. The GLC profile for fractions 7 and 8 is set forth in FIG. 1. The GLC conditions are: 10 ft.×⅛ in. 5% carbowax-TPA, column programmed at 100°-190° C. at 6° C. per minute.

The three caryophyllene alcohol isomers are trapped for infrared, nuclear magnetic resonance and mass spectral analyses. Peak 1 is confirmed as the 10,10-dimethyl-2,6-dimethylene bicyclo[7.2.0] undecan-5-ol. Peaks 2 and 3 are identified as isomers of 4,11,11-trimethyl-8-methylene bicyclo [7.2.0] undec-3-en-5-ol.

Figure 2:
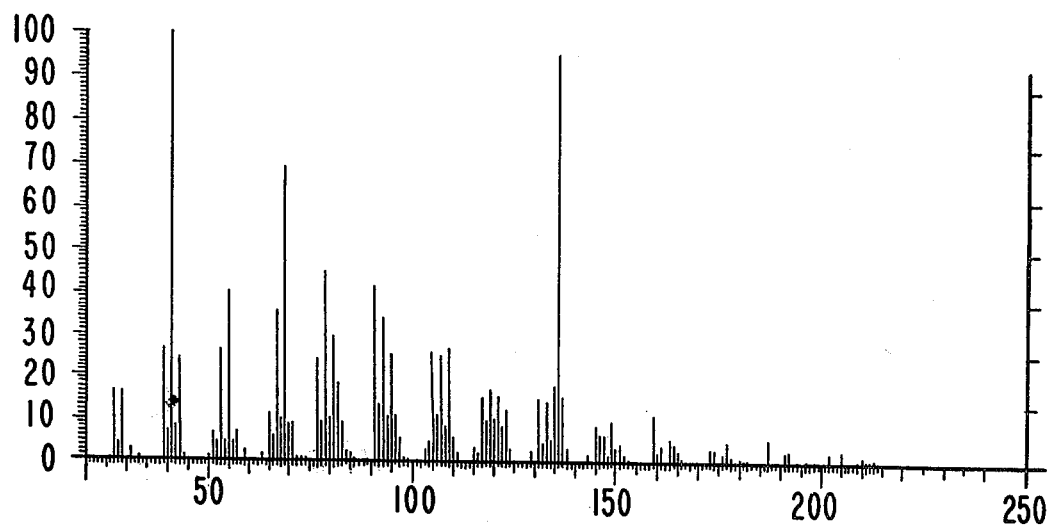
FIG. 2 is the Mass Spectrum for peak 1 of the caryophyllene alcohol mixture produced according to Example I and contains substantially all compound having the structure.

FIG. 2 is the mass spectrum for peak 1 which is confirmed as a compound having the structure:

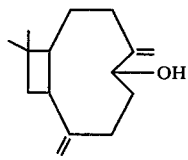

FIG. 3 is the nuclear magnetic resonance spectrum for the compound of peak 1 having the structure:

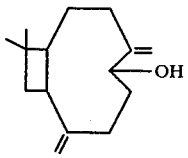

FIG. 4 is the infrared spectrum for the compound of peak 1 having the structure:

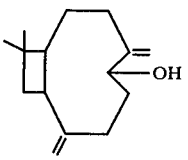

FIG. 5 is the mass spectrum for the compound having one of the structures:

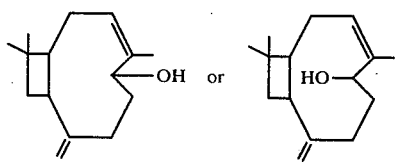

of peak 2.

FIG. 6 is the NMR spectrum for one of the compounds:

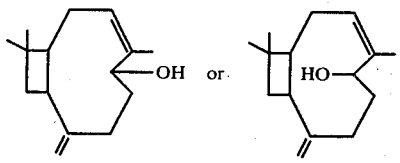

of peak 2.

FIG. 7 is the infrared spectrum for one of the compounds:

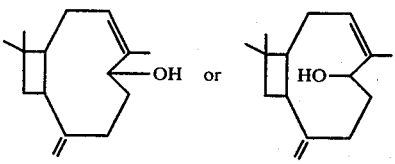

of peak 2.

FIG. 8 is the mass spectrum for one of the compounds having the structures:

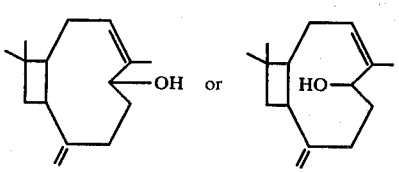

of peak 3.

FIG. 9 is the NMR spectrum of the compound having one of the structures:

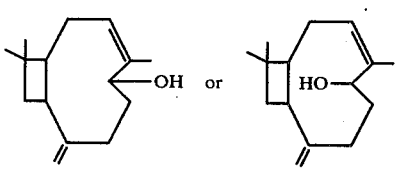

of peak 3.

FIG. 10 is the infrared spectrum for one of the compounds having one of the structures:

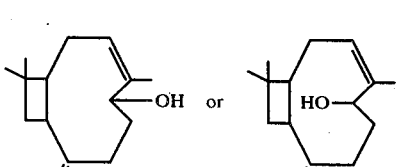

of peak 3.

Fraction 6 above is evaluated as having a sweet, woody, peppery aroma with sweet, "Vertenex-like" notes and a slight borneol background. Fraction 8 is evaluated from a foodflavor standpoint as having a musky, oriental, sandalwood-like aroma with musky, oriental and sandalwood flavor characteristics causing it to be useful in raspberry, peach, apricot and blueberry flavors at a concentration of 1 ppm.

EXAMPLE II

Preparation of Dihydrocaryophyllene Alcohol Isomer Mixture

Reaction

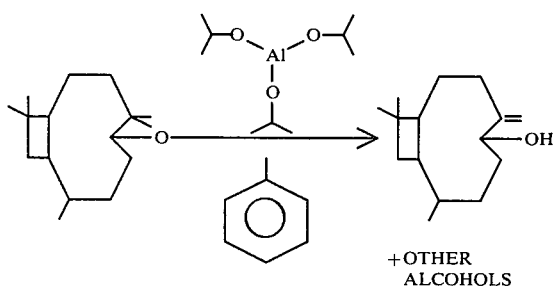

+OTHER ALCOHOLS

Chemicals

| | |
|---|---|
| Dihydro caryophyllene oxide | 91.2 g (0.41 moles) |
| Aluminum isopropoxide | 16.4 g (0.08 moles) |
| Toluene | 200 cc |
| Sulfuric acid (10% aqueous) | 100 cc |
| sodium carbonate (saturated, aqueous) | 500 cc |
| Sodium sulfate | 20 g |

Equipment 500 ml three-neck reaction flask
Mechanical Stirrer
Thermometer
Friedrichs condenser
Heating mantle The dihydrocaryophyllene oxide, half (8.2 g) of the aluminum isopropoxide and all the toluene are charged to a 500 ml flask equipped as above. The mixture is heated to reflux with stirring and monitored by use of GLC on a 10'×⅛" carbowax column at 190° C., isothermal. After four hours at reflux, another 8.2 grams of aluminum isopropoxide is added and the reaction mixture is refluxed overnight. After cooling to room temperature, 100 cc of cold 10% aqueous sulfuric acid is added and the reaction mass is stirred for 15 minutes. The organic phase is separated and the aqueous phase is extracted with two 50 cc portions of toluene. The combined organic phases are washed with water, then saturated sodium carbonate and finally water until neutral. After drying, the toluene is removed on a rotary evaporator under vacuum. The products are purified by rushover distillation on a 7 cm Vigreux column. Twelve fractions are collected. Fractions 1-5 contain a good amount of starting material. Fractions 6, 7, 8 and 9 and 10 contain product having aroma quality useful for imparting aromas to perfume compositions, perfumed articles and imparting flavor and fragrance nuances to smoking tobacco and foodstuff flavorants. Fractions 6, 7, 8 and 10 are each subjected to GLC separation yielding the following results:

| Fraction No. | Peak 1 | Peak 2 | Peak 3 | Peak 4 | Total |
|---|---|---|---|---|---|
| 6 | 13.4 | 16.7 | 37.5 | 0.8 | 77.4 |
| 7 | 13.8 | 17.8 | 42.1 | 15.2 | 88.9 |
| 8 | 12.8 | 17.4 | 49.0 | 18.0 | 97.2 |
| 10 | 10.6 | 15.1 | 54.7 | 14.1 | 94.5 |

Fraction 8 is subjectd to GLC and the GLC profile is set forth in FIG. 11. The infrared spectrum for fraction 8 is set forth in FIG. 12.

EXAMPLE III

PERFUMED SOAP

Soap bars are made up containing 100 grams each of soap chips produced according to the process of Canadian Pat. No. 1,027,718 ("Process to Manufacture Marbled and Striped Soap") quantities of 0.5 grams, 1 gram, 1.5 grams, 2.0 grams, 2.5 grams, 3.0 grams, 3.5 grams, 4.0 grams of the caryophyllene alcohol mixture produced according to Example I (fraction 6) are intimately admixed with said soap chips and the resulting slurry is heated to 150° C. using high pressure steam whereupon the resulting melts is then molded into soap cakes. Each of the soap cakes is then cooled. Each of the soap cakes manifests an excellent sweet, woody, peppery aroma with sweet borneol type undertones.

EXAMPLE IV

PERFUMED DETERGENT

Perfumed detergent prepared according to run no. 9 of United Kingdom Pat. No. 1,495,144 containing linear docecyl benzene sulfonate (sodium salt), sodium silicate and carboxymethyl cellulose optical brightener is intimately admixed at the rates of 1%, 1.5%, 2.0%, 2.5% and 3.0% by weight of the caryophyllene alcohol mixture produced according to Example I, fraction 6. After mixing, the resulting detergent manifests an excellent stable (to heat and to light) aroma which can be described as sweet, woody and peppery with a borneol undertone.

EXAMPLE V

Blueberry Flavor Formulation

The following formulation is prepared:

| Ingredients | Parts by Weight |
|---|---|
| Heliotropin | 3.0 |
| Terpinenol-4(10% in 95% aqueous food grade ethanol) | 0.2 |
| Benzaldehyde | 1.5 |
| Anisaldehyde | 0.2 |
| Phenyl acetaldehyde | 0.4 |
| Benzyl formate | 0.5 |
| Benzyl acetate | 2.0 |
| Cis-3-hexenyl benzoate (10% in 95% aqueous food grade ethanol) | 0.5 |
| Methyl hexanoate | 2.0 |
| Hexanal | 1.0 |
| Eucalytol (1% in 95% aqueous food grade ethanol) | 0.5 |
| Eugenol | 0.2 |
| Acetaldehyde | 3.0 |
| Ethyl acetate | 21.0 |
| Ethyl butyrate | 26.0 |
| Propylene glycol | 38.0 |

-continued

| Ingredients | Parts by Weight |
| --- | --- |
|  | 100.0 |

The above formulation is split into 3 portions. To the first portion is added, at the rate of 1%, the caryophyllene alcohol mixture of Example I (bulked fractions 7 and 8). To the second portion is added the dihydrocaryophyllene alcohol mixture produced according to Example II (bulked fractions 6, 7, 8 and 10). The third portion contains nothing added thereto. The formulations with and without the said caryophyllene alcohol mixture and dihydrocaryophyllene alcohol mixture are each separately combined with water at the rate of 100 parts per million. The flavor with the caryophyllene alcohol mixture and the dihydrocaryophyllene alcohol mixture prepared according to Examples I and II respectively have more oriental, sandalwood and musky characteristics and is closely similar to the flavor of wild blueberries. They are therefor preferred to the basic blueberry formulation which does not contain either of the dihydrocaryophyllene alcohol mixtures or the caryophyllene alcohol mixtures produced according to Examples I and II.

EXAMPLE VI

Raspberry Flavor Formulation

The following basic raspberry formulation is prepared:

| Ingredients | Parts by Weight |
| --- | --- |
| Vanillin | 2 |
| Maltol | 4 |
| Parahydroxy benzyl acetone | 5 |
| Dimethyl sulfide | 1 |
| Alpha-ionone (10% in propylene glycol) | 2 |
| Ethyl butyrate | 6 |
| Ethyl acetate | 16 |
| Isobutyl acetate | 14 |
| Acetic acid | 10 |
| Acetaldehyde | 10 |
| Propylene glycol | 930 |
|  | 1000 |

The above formulation is split into three parts. To the first part, at the rate of 0.3% is added the caryophyllene alcohol mixture produced according to Example I (bulked fractions 7 and 8). To the second part is added at the rate of 0.3% the dihydrocaryophyllene alcohol mixture produced according to Example II (bulked fractions 6, 7, 8 and 10). No additive is added to the third part. The three formulations are compared in water at the rate of 50 ppm. The flavors containing the caryophyllene alcohol mixture and the dihydrocaryophyllene alcohol mixture have a more ripe raspberry taste and a woody, raspberry kernel character. Therefore, the raspberry formulations containing the caryophyllene alcohol mixture and the dihydrocaryophyllene alcohol mixture have more natural like and more characteristic raspberry flavors and are therefor preferred.

EXAMPLE VII

Preparation of a Cosmetic Powder Composition

A cosmetic powder is prepared by mixing in a ball mill, 100 g of talcum powder with 0.25 g of the dihydrocaryophyllene alcohol mixture (bulked fractions 6, 7, 8 and 10) prepared according to Example II. It has an excellent sweet, woody and peppery aroma characteristic with borneol-like undertones.

EXAMPLE VIII

Perfumed Liquid Detergent

Concentrated liquid detergents (lysine salt of n-dodecyl benzene sulfonic acid as more specifically described in U.S. Pat. No. 3,948,818, issued on April 6, 1976) with intense sweet, woody and peppery aromas and borneol-like undertones are prepared containing 0.10%, 0.15%, and 0.20% of the dihydrocaryophyllene alcohol mixture produced according to Example II (bulked fractions 6, 7, 8 and 10). The detergents are prepared by adding and homogeneously mixing the appropriate quantity of dihydrocaryophyllene alcohol mixture of Example II. The detergents all possess intense sweet, woody and peppery aromas, the intensity increasing with the greater concentration of the product produced according to Example II.

EXAMPLE IX

Preparation of a Cologne and Handkerchief Perfume

The caryophyllene alcohol mixture (bulked fractions 7 and 8) produced according to Example I is incorporated into a cologne at a concentration of 2.5% in 85% aqueous ethanol. A distinct and definite sweet, woody and peppery aroma with undertones is imparted to the cologne. The caryophyllene alcohol mixture of Example I is also added to a handkerchief perfume at a concentration of 20% (in 95% aqueous ethanol) and a distinct and definite sweet, woody and peppery aroma is imparted to the handkerchief perfume.

EXAMPLE X

Tobacco Filter

Into a 20 mm cellulose filter is added the caryophyllene alcohol reaction product of Example I (bulked fractions 7 and 8) at the rate of 1,000 ppm (10 microliter of a 10% solution of said caryophyllene alcohol mixture is added to the filter). The filter is then attached to a full flavor cigarette on the market, e.g. (1) Marlboro ®, (2) Winston ® or (3) Viceroy ®, as well as on a Kentucky 1A3 reference cigarette (produced by the University of Kentucky), yielding the following results:

1. Both cigarettes containing said caryophyllene alcohol mixture, when compared to a cigarette having a filter without said caryophyllene alcohol mixture give rise to woody, cigar box-like and oriental aromas on smoking with a rather noticeable reduced harshness.

2. Both cigarettes containing said caryophyllene alcohol mixture have a lesser degree of "hotness" and give rise to a more "Turkish" oriental taste on smoking.

(1) Registered trademark of the Phillip Morris Company.
(2) Registered trademark of the R. J. Reynolds Company.
(3) Registered trademark of the Brown & Williamson Company.

EXAMPLE XI

Perfume Use of Caryophyllene Alcohol Mixture

The value of the caryophyllene alcohol mixture prepared according to Example I (bulked fractions 7 and 8) may be demonstrated in the following fragrance wherein it is used as a level of 5% by weight:

|  | A | B | C | D |
| --- | --- | --- | --- | --- |
| Linalool | 70 | 70 | 70 | 70 |
| Linalyl acetate | 20 | 20 | 20 | 20 |

-continued

| | A | B | C | D |
|---|---|---|---|---|
| Benzyl acetate | 20 | 20 | 20 | 20 |
| Citronellol | 10 | 10 | 10 | 10 |
| Geraniol | 60 | 60 | 10 | 10 |
| Phenyl ethyl alcohol | 110 | 110 | 60 | 60 |
| Hydroxy citronellal | 40 | 40 | 40 | 40 |
| Cedryl acetate | 170 | 170 | 100 | 100 |
| Eugenol | 20 | 20 | 40 | 40 |
| Sandelwood oil | 40 | 40 | 40 | 40 |
| Diethyl phthalate | 72 | 122 | 75 | 325 |
| Hexyl cinnamic aldehyde | 10 | 10 | 10 | 10 |
| Coumarin | 20 | 20 | 40 | 40 |
| Musk xylol | 40 | 40 | 40 | 40 |
| Musk ambrette | 50 | 50 | 50 | 50 |
| Bergamot oil | 13 | 13 | 20 | 20 |
| Ethyl vanillin | 4 | 4 | 4 | 4 |
| Phenyl ethyl acetate | 10 | 10 | 10 | 10 |
| Amyl salicylate | 21 | 21 | 21 | 21 |
| Benzyl salicylate | 100 | 100 | 20 | 20 |
| Patchouli oil | 50 | 50 | 50 | 50 |
| Caryophyllene alcohol mixture produced according to Example I (bulked fractions 7 and 8) | 50 | — | 250 | — |
| | 1000 | 1000 | 1000 | 1000 |

The addition of 5% caryophyllene alcohol to the above fragrance (A) gave a sweet, woody slightly peppery effect which was much more desirable than the fragrance without the caryophyllene alcohol. In particular, the dryout notes were considered much more natural.

Very interesting and valuable effects may be obtained by incorporating caryophyllene alcohol into the above formulation (C) at 25% by weight. At higher concentrations the caryophyllene alcohol contributes a more masculine and slightly more floral effect to the fragrance and is preferred over the fragrance without the caryophyllene alcohol mixture produced according to Example I (bulked fractions 7 and 8) (D).

What is claimed is:

1. A process for augmenting or enhancing the aroma of a perfume composition comprising intimately admixing with a perfume composition which additionally comprises at least one material selected from the group consisting of hydrocarbons, alcohols other than caryophyllene alcohols or dihydro caryophyllene alcohols ketones, aldehydes, nitriles, esters, lactones, synthetic essential oils and natural essential oils, from 0.005% up to 70% by weight of the perfume composition prepared by the process which consists essentially of the steps of (i) intimately admixing aluminum isopropylate, toluene and a caryophyllene derivative selected from the group consisting of caryophyllene oxide and dihydro caryophyllene oxide to form a mixture; (ii) heating the resulting mixture at a temperature of from 100° C. up to 150° C. for a period of time of from 1 up to 5 hours; and (iii) recovering rearranged caryophyllene oxide or dihydro caryophyllene oxide, a mixture of alcohols, from the reaction mass; the concentration of aluminum isopropylate catalyst in the reaction mass varying from about 0.025 molar up to about 0.75 molar and the concentration of caryophyllene oxide or dihydro caryophyllene oxide in the reaction mass varying from about 0.25 molar up to about 1.00 molar.

* * * * *